United States Patent [19]
Kirsch

[11] Patent Number: 5,052,931
[45] Date of Patent: Oct. 1, 1991

[54] ENOSSAL IMPLANT

[75] Inventor: Axel Kirsch, Filderstadt, Fed. Rep. of Germany

[73] Assignee: IMZ Fertigungs-und Vertriebsgesellschaft für dentale Technologie mbH, Fed. Rep. of Germany

[21] Appl. No.: 447,910

[22] Filed: Dec. 8, 1989

[30] Foreign Application Priority Data

Dec. 10, 1988 [DE] Fed. Rep. of Germany ....... 3841705

[51] Int. Cl.⁵ ................................................ A61C 8/00
[52] U.S. Cl. ..................................... 433/173; 433/174
[58] Field of Search ......................... 433/172, 173, 174

[56] References Cited
U.S. PATENT DOCUMENTS

| 4,011,602 | 3/1977 | Rybicki et al. | 433/173 |
| 4,552,532 | 11/1985 | Mozsary | 433/173 |
| 4,568,285 | 2/1986 | Chiaramonte et al. | 433/173 |
| 4,609,354 | 9/1986 | Koch | 433/173 |
| 4,657,510 | 4/1987 | Gittleman | 433/173 |
| 4,713,003 | 12/1987 | Symington et al. | 433/173 |
| 4,793,808 | 12/1988 | Kirsch | 433/173 |
| 4,872,839 | 10/1989 | Brajnovic | 433/173 |

Primary Examiner—John J. Wilson
Assistant Examiner—Cindy A. Cherichetti
Attorney, Agent, or Firm—Hill, Van Santen, Steadman & Simpson

[57] ABSTRACT

An enossal implant with an implantable basic structure and an implant post connected thereto characterized by the basic structure having an axial bore receiving a rigid inner sleeve which has an axial bore receiving the implant post.

13 Claims, 1 Drawing Sheet

ENOSSAL IMPLANT

BACKGROUND OF THE INVENTION

The present invention is directed to an enossal implant, which is also known as an endosteal or endosseous implant. The implant has a base structure which is firmly mounted in the bone of a jaw and has a bore for receiving an implant post on which the individual denture or structure is attached.

Numerous constructions of implants are already known. An example of a known implant structure is disclosed in my U.S. Pat. No. 4,793,808, whose disclosure is incorporated by reference thereto. These implants are used either for the fixing of individual dentures or as a support structure for bridges or the like.

European Patent Application 86 108 851.6 discloses an enossal implant whose structure has a particular advantage. This implant has a basic structure, which is implantable in the jawbone, and an implant post is then connected to this basic structure. Unfortunately, in the case of extreme stressing or loading, the implant breaks off at its statically weakest point, which is usually the transition area of the implant post between the basic structure and the denture being supported thereby. If the implant post breaks off in this way, this known structure for an implant construction is completely lost. This, consequently, involves a long and very painful extraction of the basic structure from the jawbone.

SUMMARY OF THE INVENTION

An object of the present invention is to provide an improved enossal implant in which the above-mentioned disadvantages do not occur if the implant post breaks off.

These objects are obtained by an improvement in an enossal implant which comprises an implantable basic structure and an implant post connected thereto. The improvements are that the implant post can be connected to a rigid inner sleeve which, in turn, is detachably connected in a bore of the basic structure.

Thus, if the implant post breaks off, no problems are encountered in removing the broken off post by unscrewing the inner sleeve from the basic structure. The implanted basic structure, which in may cases already has bone tissue growing therearound in an osseous manner, will not need to be removed from the jawbone. Thus, the implant post can be replaced without difficulty by inserting a new inner sleeve and an intact implant post. Preferably, the inner sleeve is provided with an external thread which is screwed into an internal thread of the bore of the basic structure. Another advantageous possibility involves a bayonet-like connection between the inner sleeve and the basic structure.

In order to be able to remove the inner sleeve as easily and as rapidly as possible from the basic structure, an upper portion of the inner sleeve advantageously is provided with radially extending blind bores for the engagement of a corresponding special wrench. For the initial insertion of the inner sleeve into the basic structure or for its removal, if the implant post has been broken within the inner sleeve, the invention further provides that the upper portion of the internal bore of the inner sleeve has a polygonal and, preferably, hexagonal internal cross section. This insures that the inner sleeve can be inserted and removed in a particularly simple manner by means of a socket wrench, such as used for socket head cap screws.

From the material standpoint, it has proved to be particularly advantageous to make the inner sleeve from the same material as the basic structure. This prevents the problem of a loosening of the connection between the basic structure and the inner sleeve due to different thermal expansion coefficients which will occur when using two different metals. Also, this avoids the risk of the formation of internal local currents in the implant, which currents may appear when two different metals are used.

According to the invention, the basic structure is provided on its outer circumference with at least one step so that the basic structure will have a tapering or smaller diameter adjacent its lower end. This downward tapering form or shape of the implant basic structure makes it adaptable in a natural form to a tooth root or can thereby be more simply fitted into an extraction hole. At the same time, through the provision of an additional external step, it is possible to make the available basic structure with different diameters at the upper end thereof, which is also necessary because the upper diameter of the extraction hole will vary as a function of the patient or dentist. In addition, as a result of the external basic structural steps, the same can have bone tissue grow positively thereto in an osseous manner.

Small cavities or depressions, such as lacunae, are preferably provided on the outer circumferential surface of the basic structure to aid in the bone tissue attaching to the base structure. These are optionally irregularly distributed cavities or depression which also engage with the jawbone when the basic structure consolidates and, consequently, insures a more reliable seating of the implant.

A particularly favorable material for the basic structure is selected from a group consisting of titanium and titanium alloys because of its limited susceptibility to the acid medium of the saliva. Advantageously, the basic structure is also externally coated with a tissue-friendly material. The most suitable coatings are proved to be plasma coatings of hydroxyl apatite, because this material is also the main constituent of the enamel of natural teeth. This material will avoid a rejection reaction of the bone tissue surrounding the basic structure.

According to the most advantageous embodiment of the invention, a spacer sleeve is provided, which can be mounted as an extension on an upper end of the basic structure. The inner sleeve is then provided with a ring-like flange or at least one radially extending projection on an upper end for engaging the spacer sleeve. A particular advantage of the spacer sleeve is that it extends the basic structure in a rigid manner up to the upper edge of the mucosa when the basic structure is being initially consolidated below the reclosing mucosa into the jawbone without any irritation caused by the deformation movements.

Preferably, the spacer sleeve has the same external diameter as the basic structure at its upper edge. Through the projection of the ring flange or at least the one projection on the upper edge of the inner sleeve which will extend over the spacer sleeve, a more secure seating thereof is insured without requiring any special shape adaptation between the basic structure and the spacer sleeve.

Advantageously, the spacer sleeve is made from electrically insulating material. Ceramic materials, such as those selected from a group consisting of aluminum oxide, magnesium oxide, zirconium dioxide, and combinations of aluminum oxide, magnesium oxide and zirconium dioxide are particularly suitable for the spacer sleeve. This is desirable so that the acid saliva does not lead to a formation of local currents in the boundary regions between the basic structure and/or the inner sleeve, on the one hand, and the spacer sleeve, on the other hand. The implant post connectible to the basic structure with the interposition of the inner sleeve is preferably constructed as an elastically deformable plastic element. This reduces the risk of relative movement between the denture and the basic structure, which, as stated hereinbefore, has led in known constructions to it being virtually impossible to separate an implant post and the basic structure from one another, particularly after the implant post has broken off. This problem is eliminated in the invention by the interpositioning of the rigid inner sleeve made from the same material as the basic structure.

Finally, the implant post can also be provided with an external thread, which is screwed into the internal thread of the inner sleeve. In addition, the implant post can also be bonded or cemented in the bore of the inner sleeve.

Other advantages and features of the invention will be readily apparent from the following description of the preferred embodiments, the drawings and claims.

DESCRIPTION OF THE PREFERRED EMBODIMENTS

Figure 1:
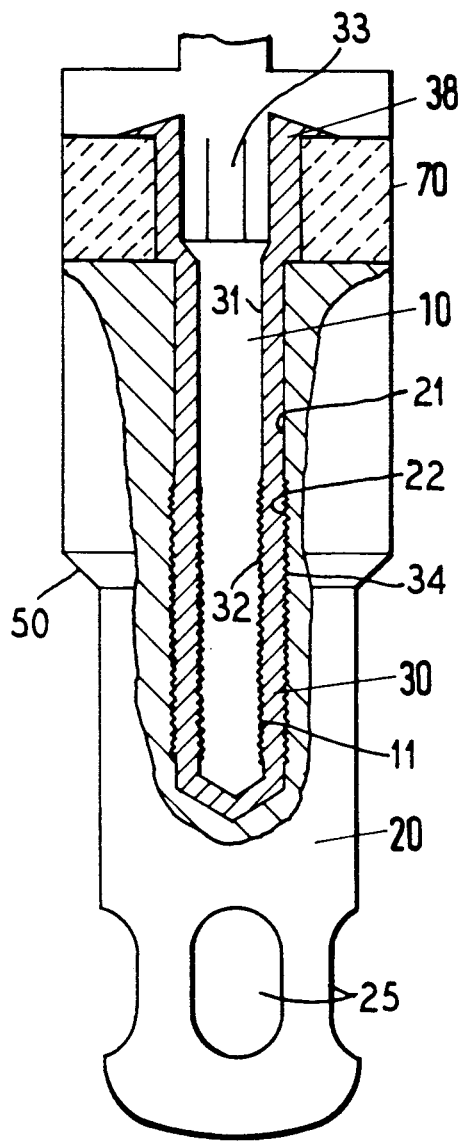
FIG. 1 is a longitudinal side view with portions broken away for purposes of illustration of the inventive implant.

The principles of the present invention are particularly useful in an implant illustrated in FIG. 1, which includes a basic structure or base member 20. On treating a patient, the basic structure 20 is inserted in an accurate fitting manner into a prepared hole in the jawbone or an extraction hole present there. The basic structure will then become consolidated or fastened within the jawbone, due to bone tissue growth in roughly three months. The basic structure 20 is preferably made from a metal selected from titanium and titanium alloys and, on its outer face, is either roughened by knurling or sandblasting or is coated with a tissue-friendly material, which is preferably a plasma coating of hydroxyl apatite. The basic structure 20 has an axial bore 21, which is opened at the top and the bore is provided with internal threads 22. An inner sleeve 30, which has external threads 34, is threaded into the bore 21 with the external threads 34 engaging the internal threads 22 of the basic structure 20. As illustrated, the basic structure 20 has a spacer sleeve 70 which has the same external diameter as the basic structure. The inner sleeve 30, on an upper end or edge, is provided with a ring-shaped flange 38 which engages an upper surface of the spacer sleeve 70 to hold the spacer sleeve on the basic structure 20. An implant post 10, which is made from elastic deformable plastic, has a shaft portion which is inserted into an internal bore 31 of the sleeve 30. As illustrated, the bore 31 is provided with internal threads 32 and the shaft portion of the implant post 10 has external threads 11 which coact with the threads 32 to hold the post in a fixed position within the sleeve 30.

The basic structure 20 tapers down from a cylindrical portion of a first diameter adjacent the sleeve 70 to a smaller diameter through a step 50. As illustrated, the step 50 is approximately between an upper third and middle third of the structure 20. The basic structure 20, in a lower third, which does not have the internal bore 21, is provided with recesses or holes 25 in order to improve the coalescence process with the jawbone. In other words, tissue can go through the openings or holes 25 to firmly lock the basic structure within the jaw.

Figure 2:
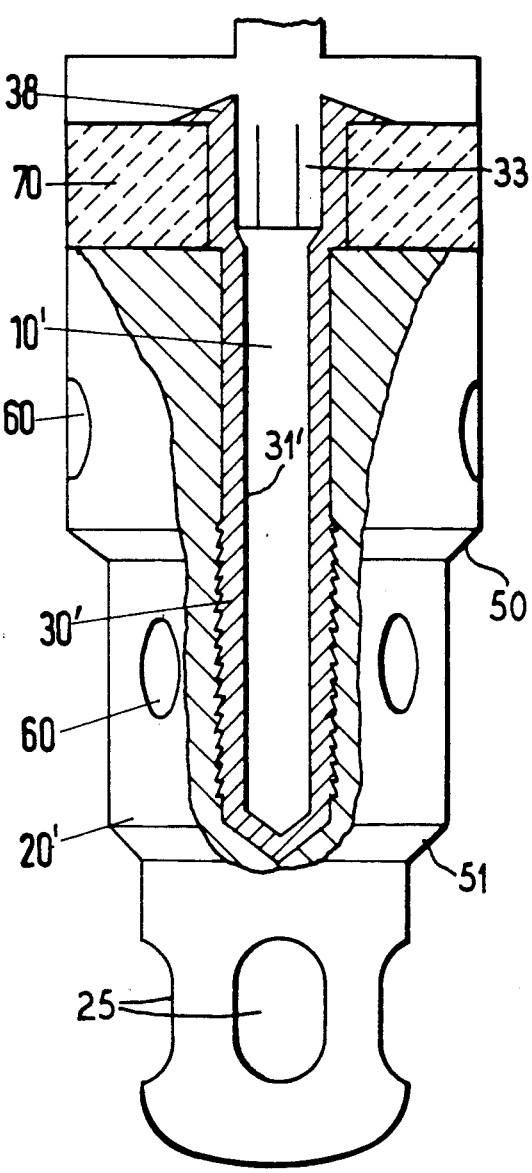
FIG. 2 is a longitudinal side view with portions broken away for purposes of illustration of a modified embodiment of the inventive implant.

An embodiment of the implant is illustrated in FIG. 2 and has a basic structure 20', which, compared with the basic structure 20 of FIG. 1, has an additional step 51 approximately separating the middle third and lower third of the structure 20'. Due to the presence of the two steps 50 and 51, the upper third or portion is of a greater diameter than the upper third of the structure 20. In the embodiment illustrated in FIG. 2, the same spacer sleeve 70 is again held by an inner sleeve 30' on an upper end of the basic structure 20'. The sleeve 30' has a smooth bore 31' in which a shaft of the implant post 10' is received and secured by being cemented in the inner sleeve 30'. The basic structure of the embodiment of FIG. 2 also is provided with depressions or so-called lacunae 60, which will improve the osseous consolidation of the bone tissue to anchor the basic structure 20' in the jaw of the patient.

Figure 3:
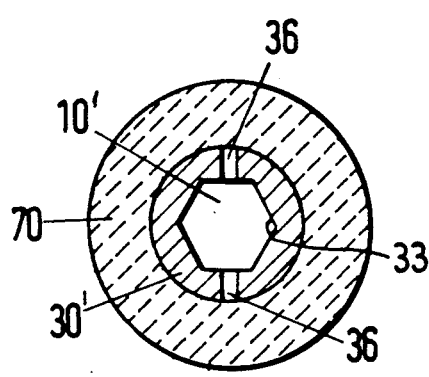
FIG. 3 is a cross sectional view through an upper marginal region of an inner sleeve according to FIG. 2.

The sleeve 30 of the first embodiment has an upper portion 33 of the bore 31, which is of a polygon shape. The sleeve 30' also has this portion 33. As best shown in FIG. 3, the portions 33 have a hexagonal internal cross-section. In addition, the sleeve, such as 30', is provided with radially extending blind holes 36 in the area of this upper portion 33, which permit the engagement of the inner sleeve with a special type of wrench. The hexagonal portion 33 can be engaged by a wrench for a socket head cap screw to insure a rapid and simple securing of the sleeve within the basic structure 20 or 20' and the removal of the inner sleeve therefrom.

Although various minor modifications may be suggested by those versed in the art, it should be understood that I wish to embody within the scope of the patent granted hereon all such modifications as reasonably and properly come within the scope of my contribution to the art.

I claim:

1. An enossal implant comprising an implantable basic structure having an axially extending bore with internal threads, a rigid inner sleeve being provided with external threads and being detachably secured in the bore of the basic structure by being threaded therein, said inner sleeve having an axially extending bore, an implant post being inserted into the axial bore of the inner sleeve to be connectible to the basic structure, said axial bore of the inner sleeve having an upper portion with engagement means for the engagement by a corresponding wrench, the basic structure and the inner sleeve being made of the same metal selected from a group consisting of titanium and titanium alloys, and a spacer sleeve being providing on an upper end of the basic structure as an extension thereof, said inner sleeve having a ring flange adjacent an upper end for engaging and holding said spacer sleeve on said basic structure, said spacer sleeve having the same external diameter as the basic structure at said upper end, and said spacer sleeve being made from an electrically insulating material selected from a group consisting of aluminum oxide, magnesium oxide, zirconium dioxide, and combinations of magnesium oxide, aluminum oxide and zirconium dioxide.

2. An implant according to claim 1, wherein the inner sleeve is connected to the basic structure in a bayonet-like manner.

3. An implant according to claim 1, wherein the basic structure has an external surface having at least two portions interconnected by a step with the smaller of said two portions being towards a lower end of the basic structure.

4. An implant according to claim 1, wherein an outer circumferential surface of the basic structure is provided with lacunae.

5. An implant according to claim 1, wherein the basic structure has an external coating of a tissue-friendly material.

6. An implant according to claim 5, wherein said coating is a plasma coating of hydroxyl apatite.

7. An implant according to claim 1, wherein the implant post is constructed as an elastically deformable plastic element.

8. An implant according to claim 1, wherein the axial bore of the inner sleeve has an internal thread and said implant post is provided with an external thread engageable on the internal thread to secure the post in said sleeve.

9. An implant according to claim 1, wherein the implant post is bonded to the axial bore of the inner sleeve.

10. An implant according to claim 1, wherein the implant post is cemented into the axial bore of the inner sleeve.

11. An implant according to claim 1, wherein the engagement means includes radially extending blind bores.

12. An implant according to claim 11, wherein the engagement means includes the upper portion of the axial bore having a polygonal internal cross section.

13. An implant according to claim 12, wherein the upper portion has a hexagonal internal cross section.

* * * * *